United States Patent
Newman et al.

(10) Patent No.: US 10,307,346 B2
(45) Date of Patent: *Jun. 4, 2019

(54) APPLIED FILMS FOR SMOOTHING WRINKLES AND SKIN TEXTURE IMPERFECTIONS

(71) Applicant: The Procter & Gamble Company, Cincinnati, OH (US)

(72) Inventors: Amanda Leigh Newman, Cincinnati, OH (US); Nancy Lorincz Leppla, Loveland, OH (US); Laurie Ellen Breyfogle, Milford, OH (US); Gordon Gerald Guay, Chelmsford, MA (US); David Edward Wilson, Reisterstown, MD (US); Joseph Michael Zukowski, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/331,473

(22) Filed: Jul. 15, 2014

(65) Prior Publication Data

US 2015/0037380 A1 Feb. 5, 2015

Related U.S. Application Data

(60) Provisional application No. 61/846,291, filed on Jul. 15, 2013.

(51) Int. Cl.
| | | |
|---|---|---|
| *A61K 8/02* | (2006.01) | |
| *A61K 8/25* | (2006.01) | |
| *A61K 8/26* | (2006.01) | |
| *A61Q 19/00* | (2006.01) | |
| *A61Q 19/08* | (2006.01) | |
| *A61K 8/04* | (2006.01) | |
| *A61K 8/06* | (2006.01) | |
| *A61Q 1/02* | (2006.01) | |
| *A45D 40/26* | (2006.01) | |

(52) U.S. Cl.
CPC .......... *A61K 8/0216* (2013.01); *A45D 40/262* (2013.01); *A61K 8/042* (2013.01); *A61K 8/062* (2013.01); *A61K 8/25* (2013.01); *A61K 8/26* (2013.01); *A61Q 1/02* (2013.01); *A61Q 19/00* (2013.01); *A61Q 19/08* (2013.01); *A61K 2800/10* (2013.01); *A61K 2800/20* (2013.01)

(58) Field of Classification Search
CPC . A61K 8/25; A61K 8/26; A61K 8/042; A61K 8/0216; A61K 8/062; A61K 2800/10; A61K 2800/20; A61Q 19/00; A61Q 1/02; A61Q 19/08; A45D 40/262
See application file for complete search history.

(56) References Cited

U.S. PATENT DOCUMENTS

| | | | |
|---|---|---|---|
| 3,755,560 A | 8/1973 | Dickert | |
| 4,421,769 A | 12/1983 | Dixon | |
| 4,965,071 A * | 10/1990 | Kawan | A61K 8/0212 424/401 |
| 4,970,252 A | 11/1990 | Sakuta | |
| 5,073,371 A | 12/1991 | Turner | |
| 5,073,372 A | 12/1991 | Turner | |
| 5,087,445 A | 2/1992 | Haffey | |
| 5,412,004 A | 5/1995 | Tachibana | |
| 5,505,937 A | 4/1996 | Castrogiovanni | |
| 5,654,362 A | 8/1997 | Schulz, Jr. | |
| 5,760,116 A | 6/1998 | Kilgour | |
| 5,811,487 A | 9/1998 | Schulz, Jr. | |
| 5,837,793 A | 11/1998 | Harashima | |
| 5,851,079 A | 12/1998 | Horstman | |
| 7,954,392 B2 | 6/2011 | Belcher | |
| 8,417,474 B2 | 4/2013 | Datta | |
| 2002/0031534 A1 | 3/2002 | Horino | |
| 2004/0009139 A1* | 1/2004 | Oldenhove | A01N 43/16 424/70.13 |
| 2005/0025558 A1 | 2/2005 | Severa | |
| 2009/0180826 A1 | 7/2009 | Guay | |
| 2009/0220436 A1* | 9/2009 | Anderson | A61K 8/8152 424/45 |
| 2010/0158829 A1* | 6/2010 | Bajor | A61K 8/42 424/59 |
| 2011/0070273 A1* | 3/2011 | Zheng | A61K 8/0204 424/401 |
| 2012/0269753 A1* | 10/2012 | Rabe | A61K 8/19 424/63 |
| 2013/0011346 A1 | 1/2013 | Tanner | |
| 2013/0164229 A1 | 6/2013 | Mendoza | |
| 2013/0189332 A1 | 7/2013 | Breyfogle | |
| 2013/0195783 A1 | 8/2013 | Breyfogle | |
| 2013/0230474 A1 | 9/2013 | Tanner | |
| 2013/0243835 A1 | 9/2013 | Tanner | |
| 2013/0243836 A1 | 9/2013 | Tanner | |

FOREIGN PATENT DOCUMENTS

| | | |
|---|---|---|
| EP | 0 244 859 | * 11/1987 |
| EP | 0244859 | 11/1987 |

(Continued)

OTHER PUBLICATIONS

U.S. Appl. No. 14/337,351, filed Jul. 22, 2014, William Robert Gately.

(Continued)

*Primary Examiner* — Blessing M Fubara
(74) *Attorney, Agent, or Firm* — John G. Powell

(57) ABSTRACT

A skin smoothing film made from a skin smoothing composition that comprises sodium silicate, polyvalent silicate and water. Moreover, the film may be made from a composition that has a contraction value of from about 30% to about 160%. The film thickness is from about 5 microns to about 50 microns, preferably from about 10 microns to about 40 microns, when applied. The standard deviation of the film over the area covered is less than about 30, preferably less than about 25.

11 Claims, 3 Drawing Sheets
(1 of 3 Drawing Sheet(s) Filed in Color)

(56) References Cited

FOREIGN PATENT DOCUMENTS

| | | | |
|---|---|---|---|
| EP | 2 404 642 A2 * | 1/2012 | |
| EP | 2404642 A2 † | 1/2012 | |
| FR | 2782269 | 2/2000 | |
| FR | 2783419 | 3/2000 | |
| JP | 6118708 | 4/1994 | |
| JP | 2009292809 A | 12/2009 | |
| WO | WO9633689 A1 | 10/1996 | |
| WO | WO97/17058 | 5/1997 | |
| WO | WO98/18431 | 5/1998 | |
| WO | WO0056270 | 9/2000 | |
| WO | WO2010129321 A | 11/2010 | |
| WO | WO2012130605 A1 | 10/2012 | |
| WO | WO2013083913 | 6/2013 | |

OTHER PUBLICATIONS

U.S. Appl. No. 14/337,358, filed Jul. 22, 2014, Rebecca Ann Finley.
"The CIE 1976 Color Difference Formulas," *Color Research Applications*, vol. 2, pp. 7-11 (1977).
"Instant Eye Tightener", Advanced Health UK; Eye Secrets; Record ID 1459260; GNPD; MINTEL, Dec. 31, 2010.
"Instant Line Smoother", Beauty Solutions USA; Fran Wilson AgeLess Express; Record ID 1520054; GNPD; Mintel, Apr. 30, 2011.
Kokini J L et al: "Storage stability of model sucrose or salt added O/W emulsions through steady shear and creep rheological measurements", A Journal of Food Processing and Preservation, Trumbull, CT, US, vol. 12, Jan. 1, 1989.
Craig Bonda: "Research Pathways to Photostable Sunscreens". Cosmetics & Toiletries. Wheaton. IL. US vol. 123, No. 22 Feb. 1, 2008.
International Search Report PCT/US2014/047437; dated Nov. 24, 2014.
International Search Report PCT/US2014/047437; dated Feb. 18, 2015; 16 pages.
International Search Report PCT/US2014/047431; dated Nov. 24, 2014; 13 pages.
International Search Report PCT/US2014/046647; dated Dec. 9, 2014.

\* cited by examiner
† cited by third party

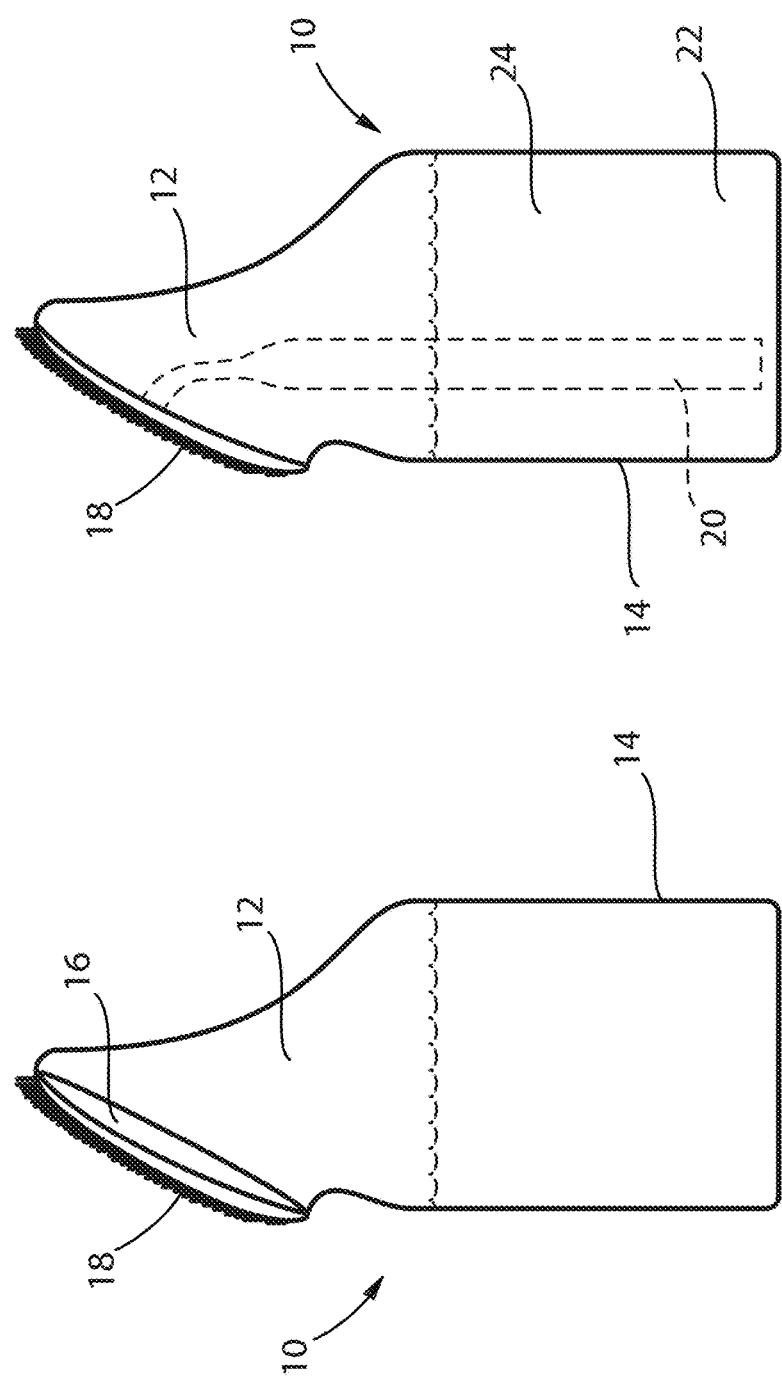

APPLIED FILMS FOR SMOOTHING WRINKLES AND SKIN TEXTURE IMPERFECTIONS

FIELD OF THE INVENTION

The present invention relates to films of personal care compositions, and methods of applying the films, which exhibit adhesion and contraction of skin to smooth and flatten wrinkles and texture imperfections.

BACKGROUND OF THE INVENTION

Visible wrinkles, particularly those on the face and around the eyes, are one of the most prevalent and undesirable signs of aging. Many consumer products and procedures are devoted to hiding or reducing wrinkles. These products and procedures can be simple and inexpensive, for example, applying make-up, particularly a primer or colored foundation, to simply cover the wrinkles on a consumer's skin. Far more expensive and drastic procedures, such as surgical face lifts and Botox injections are also used to reduce the appearance of wrinkles on the face. There are a plethora of lotions and creams which purport to hydrate the skin making it more supple and reducing the appearance of wrinkles. Some of these liquid products contain active ingredients, for example niacinamide, that help repair and rejuvenate skin over time. All of these products and procedures have drawbacks.

Foundation and other make-up products are often visible, offer minimal texture benefits, and have no lasting effect on the skin. Once the make-up is removed, the skin is the same in appearance as before the make-up was applied. Liquid products can have chronic, acute or both effects on the skin. Hydration and optical effects are common acute benefits, and these benefits wear-off over time. Chronic actives may rejuvenate or repair the skin over time. These chronic benefits take time to occur and are incremental improvements. There are limits to how effective these chronic benefits can be. Plastic surgery and injections of chemicals have a more pronounced, immediate and dramatic effect on the look of a consumer's skin, but these procedures can be very expensive and come with many risks. Plastic surgery has the same risk of failure as any other surgical procedure, including disfigurement.

Attempts have been made to develop new categories of products to improve the appearance of skin without the drawbacks of existing products and procedures. One such family of products can be generally classified as "adhesive, contractile film formers". Film formers are chemical compositions that when applied to skin, leave a pliable, cohesive and continuous covering. A select group of film formers are also adhesive to skin and even contractile. Wrinkles, in their simplest form, are crevices or valleys in the skin. When an adhesive, contractile film former is applied, the skin at the bottom of the valley or crevice may be pulled to the surface, causing skin look smooth and wrinkle-free. The drawbacks of existing adhesive, contractile film forming products include discomfort caused by the contraction of the skin, irritation of the skin, cracking of the film as the consumer uses her face muscles, incompatibility with other cosmetic products in her regimen, and visibility of the film which is often whitish and noticeable. Curing or reducing one of these problems has, in the past, exacerbated one of the other problems.

Sodium silicate is an adhesive, contractile film forming ingredient used today. High levels of sodium silicate can result in high to moderate skin contraction, resulting in high to moderate immediate wrinkle reduction. Unfortunately, however, the more sodium silicate used, the more skin irritation observed and the more brittle (less durable) the dried film. One skilled in the art may attempt to use plasticizers to combat the problem of a brittle film, however, as stated above resolving this issue exacerbates others—in this case whiteness increases and contraction is reduced. Thus, these solutions are not acceptable to the consumer.

It has further been determined that when contracting films are applied to skin the thickness and evenness of the film is very important to its performance. Finger application has been the standard for applying such films in the past, although some mechanical applicators exist. Neither human fingers nor commercially used applicators are affective for applying a uniform film of a single desired, optimal thickness. Current applicators and finger application result in a splotchy application with areas that are both undesirably too thickness and too thin.

Applicators for cosmetics and skin cream are well known. But contracting films are intended to be invisible, and accordingly they are generally applied clear and dry clear. The tightening results are intended to be visible, but the film itself is intended to be invisible. Thus, the applicator (which is typically a human finger), is important because the applied film cannot be seen. Moreover, thickness and uniformity of the applied film is critical to the films performance. Contrast that to applicators used for make-up and other cosmetics. Make-up can be seen as it is applied. Where it is applied it is visible, and the amount, that is thickness, can also be seen. The uniformity is visible as well, and often non-uniformity is intentionally applied, for example, make-up can be feathered around the edges to reduce its visibility. Moreover, the thickness of the applied film is a matter of preference, not performance, i.e., some women use more make-up than others but the make-up works the same regardless of how it is applied. Thus, the use of applicators for cosmetics and skin cream, is substantially different than the use of an applicator to apply an invisible film in a specific thickness uniformly over the desired area.

Thus, there is a continuing desire to provide applicators that can apply compositions that can improve the appearance of skin, more specifically, reduce the appearance of wrinkles on skin, while balancing the correct amount of skin contraction, film flexibility, lack of film whiteness, contraction resiliency, compatibility with other cosmetic products, and lack of skin irritation. These and other improvements over the art are provided by the present invention.

SUMMARY OF THE INVENTION

There is provided a skin smoothing film comprising a skin smoothing composition that comprises sodium silicate, polyvalent silicate and water, or has a contraction value of from about 30% to about 160%, or both. The film thickness being from about 5 microns to about 50 microns, preferably from about 10 microns to about 40 microns, and even more preferably from about 10 microns to about 30 microns, when applied. The standard deviation of the film when measured over at least 80% of the area covered is less than about 30, preferably less than about 25 and even more preferably less than about 20. The skin smoothing film may be produced by applying a skin smoothing composition with a human finger or an applicator.

The films of this invention may comprise a skin smoothing composition that has from about 0.5 to about 4% sodium silicate as measured by silica content ($SiO_2$) and from about 0.1% to about 4.0% of a polyvalent silicate. The compositions of this invention may comprise at least one plasticizer present in the composition at from about 1% to about 20%, by weight. Additionally, the levels of sodium silicate, polyvalent silicate, and plasticizer are to be balanced according to these ratios (a) sodium silicate ($SiO_2$) to polyvalent silicate ratio equal to or greater than 0.7, and/or (b) total silicate (sodium silicate+polyvalent silicate) to total plasticizer ratio equal to or less than 1.8. The composition is provided in a carrier, for example, from about 10 to 98% water, and can be in the form of a water-based formulation, such as a water gel, oil-in-water emulsion, or a composition comprising one or both of these forms.

In one aspect of this invention the sodium silicate has a molar ratio of $SiO2:Na2O$ ratio of 3.3 or less, and the polyvalent silicate is a silicate clay selected from the group consisting of bentonite, laponite, smectite, and kaolinite. It is preferred that the polyvalent silicate is stable at a pH of greater than 10. The plasticizer can be, for example, an alkyl mono-glycol or di-glycol containing 3 to 5 carbon atoms. Further, the plasticizer can be propylene glycol.

According to in vitro tests predictive of in vivo performance, the compositions of this invention exhibit contraction from about 0.2 to about 0.9 inches, whiteness equal to or lower than 40, loss of contraction equal to or lower than 20%, and polar component surface energy equal to or lower than 35 $\gamma p/mJ/m^2$. Further, the films formed by the compositions of the present invention exhibit a balance of all factors mentioned in the previous sentence, which can be expressed using a multivariable equation such as performed in calculating the Overall Performance Score, which is lower than 2.8 for consumer preferred executions.

In response to the technical problems identified in the Background of The Invention, the present invention provides films with excellent initial and lasting contraction, are flexible, transparent, and non-irritating. Further forms of the present invention will be appreciated in the detailed description that follows.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

The patent or application file contains at least one drawing executed in color. Copies of this patent or patent application publication with color drawings/photographs will be provided by the Office upon request and payment of the necessary fee.

In the drawings:

FIG. 1 is a schematic drawing of an applicator suitable for applying skin smoothing compositions in accordance with the present invention;

FIG. 2 is a cross sectional view of the applicator of FIG. 1;

FIG. 3 is a graph of the pixel v. grey value for one consumer applying a film with their finger and an applicator of the present invention;

FIG. 4 is a graph similar to FIG. 3 but with a different consumer;

FIG. 5 is a picture of a film according to the present invention on a skin mimic substrate; and, FIG. 6 is a picture of a film applied on a skin mimic surface with the finger of the same consumer who produced the film of FIG. 5.

DETAILED DESCRIPTION OF THE INVENTION

Figure 3:
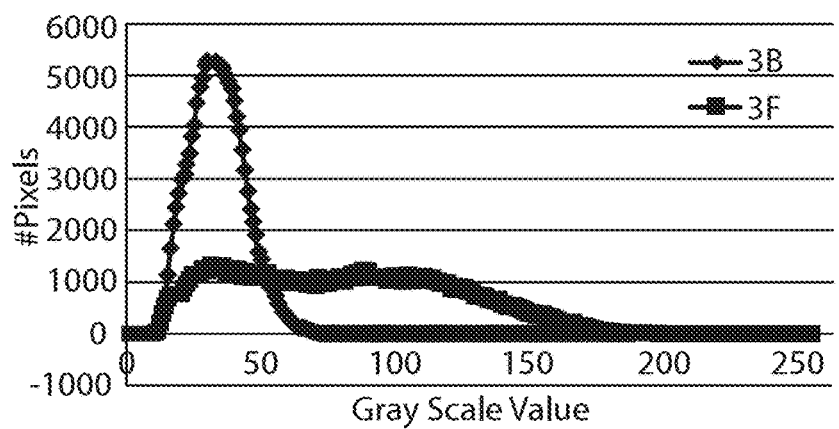

All percentages and ratios used herein are by weight of the total composition and all measurements made are at 25° C., unless otherwise designated. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

The term "apply" or "application" as used in reference to a composition, means to apply or spread the compositions of the present invention onto a substrate such as the human skin surface or epidermis.

The term "dermatologically acceptable" as used herein means that the compositions or components described are suitable for use in contact with human skin tissue without undue toxicity, incompatibility, instability, allergic response, and the like.

The term "safe and effective amount" as used herein means an amount of a compound or composition sufficient to significantly induce a positive benefit.

The term "facial skin surface" as used herein refers to one or more of forehead, periorbital, cheek, perioral, chin, and nose skin surfaces. While facial skin surfaces are of concern and are exemplified herein, other skin surfaces may be treated with the compositions of the present invention, for example, surfaces typically not covered by clothing such as facial skin surfaces, hand and arm skin surfaces, foot and leg skin surfaces, and neck and chest skin surfaces (e.g., décolletage).

The terms "stable" and "stability" as used herein mean a composition which is substantially unaltered in chemical state, physical homogeneity and/or color when the composition is at a temperature of from about 1° C. to about 40° C.

Applicator and Applied Films

The thickness, uniformity and area of application of the skin smoothing films of this invention are all important to performance of the film itself. But measuring the thickness and uniformity of a clear, substantially invisible film is a technical challenge. A new test method was developed to measure these important parameters. Specifically, a fluorescent material was added to the compositions of this invention, and comparative compositions. The fluorescent enhanced compositions were then applied to a variety of substrates which were then carefully photographed. The photographs were visually inspected and graded, and they were mechanically graded as well, using commercially available analytical tools. These test, which are explained in more detail below, were performed on four substrates: 1) under and around the human eye; 2) the smooth, generally hairless portion of the human forearm; 3) skin mimic material; and, 4) Leneta cards. While the specific results for the application of these films on the four surfaces varied because the surfaces varied (which would be expected) the general trends of film thickness and uniformity, as well as the area covered, are essentially the same regardless of the substrate. And those trends are, regardless of the substrate, hard tip applicators with no coating (as determined by Shore A durometer) and fingers generally apply non-uniform films. Soft tip and coated applicators apply a much more uniform film. Within applicators, a hard tip applicator with no coating is not as good as an applicator with a soft tip and applicators with soft or hard tips having a portion of its surface coated with flock fibers, bristles, cloth, sponge, polymeric mesh, nonwovens, and mixtures thereof. More specifically, the applicator head may be coated with fibers, foam, cotton, a roller ball or any other suitable material that may releasably hold the composition. For example these may include, but are not limited to those described in published US Patent Application 2005/0025558 A1, to Raymond J. Severa, which application is assigned to Bonne Bell, Inc. or U.S. Pat. No. 5,851,079, to Richard L. Horstman, which application is assigned to The Procter & Gamble Co. One preferred foam for use in any applicator described herein is the gradient foam described in published US Patent Application 2009/0180826 A1, to Gordon Guay, which application is assigned to The Procter & Gamble Co.

Referring now to FIG. 1 where applicator 10 comprises body 14 and head 12. In this embodiment head 12 has two coatings, underlayment 16 and outer layer 18. Those skilled in the art will appreciate that one layer of coating material may be sufficient, three or more layers may be used. Appropriate coating materials are listed directly above, and other materials, as well as combinations thereof, will be apparent to those skilled in the art. And as stated above, a "soft" tip applicator may be used without coating. Preferred heads for use in the present invention have a Shore A Durometer softness of from about 25 to about 140, preferably from about 30 to about 100, and even more preferably less than about 70. The head can be made of any of variety of materials to produce the desired softness, specifically, thermoplastic elastomers, plastics, foams and sponge materials like SBR, NBR, polyethylene foams, and polyurethane foams. The surface area of the coating on the tip is preferably from about 5.0 cm$^2$ to about 0.3 cm$^2$.

Outer layer 18 on head 12 of applicator 10 is shown as a flock material. Flock coatings are commercially available from Companies like JFA Flock. Preferably head 12 has a portion of its surface coated with flock fibers, wherein the flock fibers have a Denier from about 3.5 dtex to about 1.5 dtex, preferably about 2.0 dtex to about 0.7, even more preferably less than about 1.8 dtex, and a flock fiber length of from about 2.0 mm to about 0.3 mm. Denier is an industry standard measurement of flock/fiber diameter that is known to those skilled in the art.

The flock may be any natural or synthetic material. Examples of suitable materials include, but are not limited to, starch, polyolefins (e.g., polyethylene and polypropylene), polyamides (e.g., Nylon™ 6-12, Nylon™ 6, polyphthalamide), cotton, Kevlar™, NPBT, acetal resins, polyesters (e.g., PET, PBT), fluoropolymers (e.g., PVDF, PTFE), polyacrylates, polysulfones, and mixtures thereof. Other suitable polymeric materials include thermoplastic elastomers such as polyetheramides (e.g., Pebax™), polyurethanes Pellethane™), polyolefin elastomers (e.g., Santoprene™), styrene-ethylene-butylene-styrene block copolymers, styrene-butadiene-styrene block copolymers, styrene-isoprene-styrene block copolymers (e.g., Kraton™ rubbers), and combinations thereof. These polymeric materials may contain fillers and additives to provide strength, lubricity, texture, abrasiveness, and color to the flock surface. Examples of suitable fillers and additives include, kaolin. FIFE, titanium dioxide, and the like.

In addition to the main flock fiber, specialty fibers can be used to provide an added functionality to the applicator. Examples of unique fibers which can be incorporated into the filaments include super-absorbent fibers, abrasive fibers, and slippery fibers. Any type of fiber capable of being produced can be used as a short fiber for surface texturization. These short flock fibers can vary in length and denier. The range of fiber lengths suitable for electrostatic coating ranges from 0.762 mm to 6.35 mm (0.03" to 0.25"). Fiber diameters can range from 0.1-100 denier. In addition, numerous types of materials in particle form can be applied including various types of micronized abrasives, Teflon™, and salts.

FIG. 2 shows a cross sectional view of applicator 10 to show the body interior 24 of body 14 which contains skin smoothing composition 22 and fluid communication channel 20. Skin smoothing composition 22 can flow from body 14 to head 12 and on to outer layer 18 via fluid communication channel 20. Other mechanical methods of moving fluid from body 14 to outer layer 18 will be known to those skilled in the art. Moreover, it is understood that the applicators of the present invention can be supplied without fluid. The consumer can simply dip the head of the applicator into a fluid and then apply that fluid to their skin as desired.

The applicators of the present invention deposit a more uniform film of an optimal thickness. Consumers using their fingers were not able to reproduce the film uniformity results when compared to the applicators disclosed herein. While the thickness of a clear film on skin is difficult to measure, the applicants were able to develop a new test method to accurately measure the thickness and uniformity of an applied film. Specifically, a florescent composition, Tinopal CBS-X (purchased from BASF) was added to the compositions of the present invention and the comparative compositions as well. Films of know/controlled thickness were created and evaluated for brightness of the florescent composition. Then calibration curves were created that are used to convert the florescence (measured as grey scale, described below) to thickness of the applied film.

More specifically, 0.07%, by weight, of Tinopal CBS-X was added to the composition of Example 1 below, and then applied to a Leneta Card (Form 2A) using BYK Drawdown Bar film applicators to apply wet films of known thickness, 25.4 µm, 50.8 µm and 76.2 µm. These films were allowed to dry and then evaluated. The films were illuminated using a xenon flash through a 450 nm band pass filter and captured using a Digital SLR with a Wratten #8 yellow filter installed on the lens to filter incident light. The resulting image was evaluated by measuring the gray value of the fluorescence in the green channel of the RGB image. A standard curve of film thickness verse fluorescence was determined from these formulation draw downs.

After the test was developed and calibrated, consumers were brought in to test the human application and film creation. As stated above, numerous substrates were tested, including two different areas of human skin. As discussed above, the absolute test results may vary depending on the substrate used, the trends for uniformity and thickness are the same regardless of substrate. And normalized values, such as the standard deviation, remain the same regardless of the substrate tested. By way of example, a test using a polyurethane skin mimic material is described herein. Skin mimics are known to those in the art, and the ones used herein are made by the methods described in U.S. Pat. Nos. 7,954,392 B2 and 8,417,474 B2.

Consumers were directed to apply 2 μl/cm2 over a 3×4 cm area onto a skin mimic material with their finger, and then a new 3×4 cm skin mimic was applied with the same material in the same amount using an applicator according to the present invention. These same consumers were asked to apply compositions with fingers and applicators on their skin and on Leneta cards with substantially similar results, the skin mimic data was used because it was the most consistent across consumers. As often happens with human trials, at least one consumer failed to follow directions and the data for both finger and applicator was unusable. Consumers were instructed to cover the entire area using 10 strokes. Utilizing a consistent masking area, each pixel's gray scale value was determined as described above. The average gray scale value and standard deviation of the masked pixels for each panelist was determined for the finger application and applicator application. The standard deviation was calculated using commercially available statistical software JMP, by SAS Institute. Smaller standard deviations are indicative of more uniform or more even film thickness.

Figure 4:
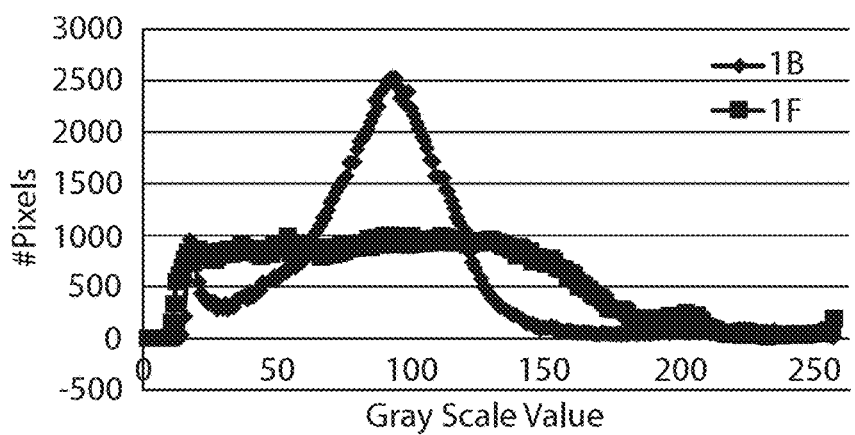

FIGS. 3 and 4 show test results from two consumers in a study comparing film thickness and uniformity for a film applied by their finger and with an applicator according to the present invention which had a portion of the head covered with flock. The film was a mixture of the composition according to Example 1 below with Tinopal CBS-X. The pixels in the coated area were evaluated for brightness, and reported on the X-Axis as a grey scale value using appropriate image analysis software. Zero on the grey scale is a black spot with no coverage. 250 on the grey scale is a bright, thick portion of the film. The number of pixels that comprise a particular grey value is shown on the Y-Axis. The blue lines in each of FIGS. 3 and 4 are the film created with an applicator according to this invention, and the red lines are from the film applied by the finger. While consumers in this test applied films to their skin, Leneta cards and skin mimics, this data is from the skin mimic material. Again, as you move from 0 to 250 along the X-Axis, the film thickness increases.

The sharp spike in the blue lines of FIGS. 3 and 4 indicate a large grouping of pixels around a specific grey value (approximately 40 in FIG. 3 and approximately 100 in FIG. 4). This would indicate that the films represented by the blues lines is substantially uniform in thickness. Again, the blue lines represent a film created an applicator of the present invention. This is sharp contrast to the red lines which are flat and span a broad range of grey scales which indicates a broad range of thicknesses. The Standard deviations for FIGS. 3 and 4 are:

|        | Blue | Red |
|--------|------|-----|
| FIG. 3 | 10   | 41  |
| FIG. 4 | 36   | 51  |

Figure 5:
Figure 6:
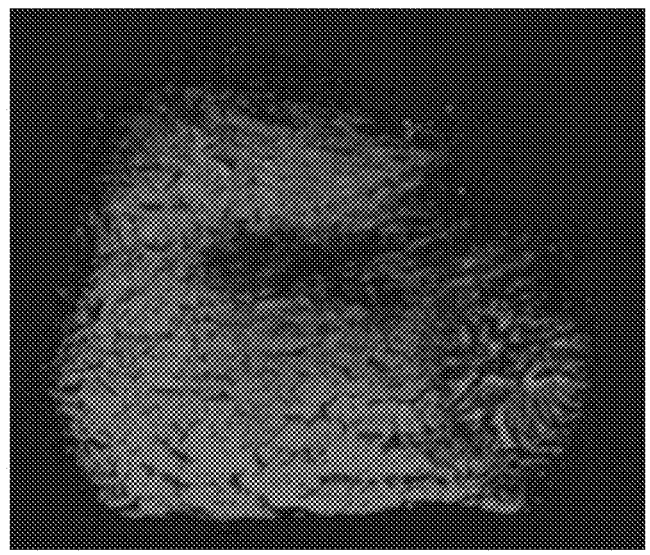

FIGS. 5 and 6 are the actual photographs for one consumer in this study for illustrative purposes. FIG. 5 was applied with an applicator (and used to generate a blue line as shown in FIGS. 3 and 4) and FIG. 6 is a picture of the film applied by a finger (and used to generate a red line). It is quite clear from these graphs, and the statistical analysis of this data, that using an applicator is far superior to applying the films of this invention with the human finger. This test was also used to determine the optimal parameters and materials for the applicators of this invention.

Compositions

The present invention relates to various compositions and, more specifically, to compositions for application to a skin surface. The compositions may be in a wide variety of product forms that include, but are not limited to, solutions, suspensions, lotions, creams, gels, toners, sticks, pencil, sprays, aerosols, ointments, cleansing liquid washes and solid bars, pastes, foams, powders, mousses, wipes, strips, patches, hydrogels, film-forming products, facial and skin masks (with and without insoluble sheet), make-up such as foundations, eye liners, and eye shadows, and the like. The composition form may follow from the particular dermatologically acceptable carrier chosen, if present in the composition.

Film Forming Composition

The skin smoothing compositions of this invention comprise from about 0.5 to about 4% sodium silicate as measured by silica content ($SiO_2$) and from about 0.1% to about 4.0% of a polyvalent silicate. The polyvalent silicate is an silicate clay selected from the group consisting of bentonite, laponite, smectite, and kaolinite. It is preferred that the polyvalent silicate is stable at a pH of greater than 10.0. Preferred film forming compositions form a non-tacky film which is removable with water used with cleansers such as soap. The ratio silica to polyvalent silicate is preferably from about 0.70 to about 4.0, more preferably from about 1.0 to about 3.0, even more preferably from about 1.0 to about 2.0. It is preferred the overall film forming composition has a pH of 10.0, more preferably greater than 10.5, and even more preferably greater than 11.0.

In addition to the silica and polyvalent silicate film formers of the present invention, the film forming composition can optionally comprise film forming polymers. Examples of suitable optional film forming polymeric materials include:

a) sulfopolyester resins, such as AQ sulfopolyester resins, such as AQ29D, AQ35S, AQ38D, AQ38S, AQ48S, and AQ55S (available from Eastman Chemicals);

b) polyvinylacetate/polyvinyl alcohol polymers, such as Vinex resins available from Air Products, including Vinex 2034, Vinex 2144, and Vinex 2019;

c) acrylic resins, including water dispersible acrylic resins available from National Starch under the trade name "Dermacryl", including Dermacryl LT;

d) polyvinylpyrrolidones (PVP), including Luviskol K17, K30 and K90 (available from BASF), water soluble copolymers of PVP, including PVP/VA S-630 and W-735 and PVP/dimethylaminoethylmethacrylate Copolymers such as Copolymer 845 and Copolymer 937 available from ISP, as well as other PVP polymers disclosed by E. S. Barabas in the Encyclopedia of Polymer Science and Engineering, 2 Ed. Vol. 17 pp. 198-257;

e) polyurethanes, including Polyderm PE-PA, available from Alzo International Inc.;

f) co-polymerized amido ester compounds, including Polyderm PPG-17, available from Alzo International Inc.;

g) acrylic latex dispersions;

h) high molecular weight silicones such as dimethicone and organic-substituted dimethicones, especially those with viscosities of greater than about 50,000 mPas;

i) high molecular weight hydrocarbon polymers with viscosities of greater than about 50,000 mPas;

j) polysaccharide gums such as xanthan gum, dehydroxanthan gum, cellulose derivatives, crosslinked-xanthan gum, hydroxypropyl xanthan gum, undecylenoyl xanthan gum, deacetylated xanthan gum, guar gum, cellulose gum, carrageenan, hydroxylpropyl methyl cellulose, and sodium carboxymethyl chitin;

k) organosiloxanes, including organosiloxane resins, fluid diorganopolysiloxane polymers and silicone ester waxes.

Examples of these optional polymers are found in PCT publication Nos. WO96/33689, published Oct. 31, 1996; WO97/17058, published May 15, 1997; and U.S. Pat. No. 5,505,937 issued to Castrogiovanni et al. Apr. 9, 1996, all incorporated herein by reference. Additional film forming polymers suitable for use herein include the water-insoluble polymer materials in aqueous emulsion and water soluble film forming polymers described in PCT publication No. WO98/18431, published May 7, 1998, incorporated herein by reference. Examples of high molecular weight hydrocarbon polymers with viscosities of greater than about 50,000 mPas include polybutene, polybutene terephthalate, polydecene, polycyclopentadiene, and similar linear and branched high molecular weight hydrocarbons.

Optional film forming polymers include organosiloxane resins comprising combinations of $R_3SiO_{1/2}$ "M" units, $R_2SiO$ "D" units, $RSiO_{3/2}$ "T" units, $SiO_2$ "Q" units in ratios to each other that satisfy the relationship $RnSiO_{(4-n)/2}$ where n is a value between 1.0 and 1.50 and R is methyl. Note that a small amount, up to 5%, of silanol or alkoxy functionality may also be present in the resin structure as a result of processing. The organosiloxane resins must be solid at about 25° C. and have a molecular weight range of from about 1,000 to about 10,000 grams/mole. The resin is soluble in organic solvents such as toluene, xylene, isoparaffins, and cyclosiloxanes or the volatile carrier, indicating that the resin is not sufficiently crosslinked such that the resin is insoluble in the volatile carrier. Particularly preferred are resins comprising repeating monofunctional or $R_3SiO_{1/2}$ "M" units and the quadrofunctional or $SiO_2$ "Q" units, otherwise known as "MQ" resins as disclosed in U.S. Pat. No. 5,330,747, Krzysik, issued Jul. 19, 1994, incorporated herein by reference. In the present invention the ratio of the "M" to "Q" functional units is preferably about 0.7 and the value of n is 1.2. Organosiloxane resins such as these are commercially available such as trimethylsiloxysilicate/cyclomethicone D5 Blend available from GE Toshiba Silicone, Wacker 803 and 804 available from Wacker Silicones Corporation of Adrian Mich., KP545 from Shin-Etsu Chemical and G. E. 1170-002 from the General Electric Company. In the present invention, by having film forming polymer mainly in the second layer, the film forming polymer will exist in a higher concentration at a localized area, and thereby forming a film of higher film intensity when applied to the skin, compared to the remainder of the composition. Such concentrated area of high film intensity provides improved adhesion of the entire composition to the skin. Namely, by providing the film forming polymer mainly in the second layer, the amount of film forming polymer included in the entire composition can be reduced, or if the same amount of film forming polymer is formulated in the second layer, an entire composition having improved adhesion is obtained. In a preferred embodiment, the content level of film forming polymer in the second layer is from about 0.1% to about 20%, preferably from about 0.5% to about 10%, more preferably from about 1% to about 8%.

Plasticizer

The compositions of this invention may comprise at least one plasticizer present in the composition at from about 1% to about 20%, preferably from about 1% to about 15%, more preferably 2% to about 10% by weight. The plasticizer can be, for example, an alkyl mono-glycol or di-glycol containing 3 to 5 carbon atoms. Further the plasticizer can be propylene glycol. The plasticizers herein are selected from the group consisting of polyhydric alcohols, water soluble alkoxylated nonionic polymers, and mixtures thereof. Polyhydric alcohols useful herein include glycerin, propylene glycol, 1,3-butylene glycol, 1,3 propanediol, dipropylene glycol, diglycerin, sodium hyaluronate, polypropanediol and mixtures thereof.

Commercially available plasticizers herein include: glycerin available from Asahi Denka; propylene glycol with tradename LEXOL PG-865/855 available from Inolex, 1,2-PROPYLENE GLYCOL USP available from BASF; 1,3-butylene glycol available from Kyowa Hakko Kogyo; dipropylene glycol with the same tradename available from BASF; 1,3 propane diol with tradename ZEMEA from DuPont Company; polypropanediol with tradename CERENOL H250 from DuPont Company, diglycerin with tradename DIGLYCEROL available from Solvay GmbH; sodium hyaluronate with tradename ACTIMOIST available from Active Organics, AVIAN SODIUM HYALURONATE series available from Intergen, HYALURONIC ACID Na available from Ichimaru Pharcos.

Dermatologically Acceptable Carrier

The compositions of the present invention may also comprise a dermatologically acceptable carrier (which may be referred to as "carrier") for the composition. The phrase "dermatologically acceptable carrier", as used herein, means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. Non-limiting examples include simple solutions (e.g., aqueous, organic solvent, or oil based), emulsions, suspensions, and solid forms (e.g., gels, sticks, flowable solids, or amorphous materials). In certain embodiments, the dermatologically acceptable carrier is in the form of an emulsion or suspension. Emulsion or suspension may be generally classified as having a continuous aqueous phase (e.g., oil-in-water and water-in-oil-in-water) or a continuous oil phase (e.g., water-in-oil and oil-in-water-in-oil). The oil phase of the present invention may comprise silicone oils, non-silicone oils such as hydrocarbon oils, esters, ethers, and the like, and mixtures thereof.

Emulsions may further comprise an emulsifier. The composition may comprise any suitable percentage of emulsifier to sufficiently emulsify the carrier. Suitable weight ranges include from about 0.1% to about 10% or about 0.2% to about 5% of an emulsifier, based on the weight of the composition. Emulsifiers may be nonionic, anionic or cationic. Suitable emulsifiers are disclosed in, for example, U.S. Pat. No. 3,755,560, U.S. Pat. No. 4,421,769, and *McCutcheon's Detergents and Emulsifiers*, North American Edition, pages 317-324 (1986). Suitable emulsions may have a wide range of viscosities, depending on the desired product form. The carrier may further comprise a thickening agent as are well known in the art to provide compositions having a suitable viscosity and rheological character.

Pigments and Powders

The compositions of the present invention can comprise from about 5% to about 45%, preferably from about 5% to about 30% of a pigment powder component. The pigments included in the pigment powder component herein may be hydrophobic in nature, or hydrophobically treated. By keeping the level of pigment component low, the entire composition maintains flexibility to accommodate other components which provide spreadability, moisturization, and fresh and light feel. The species and levels of the pigments are selected to provide, for example, shade, coverage, good wear performance, and stability in the composition.

Pigments useful for the pigment component herein are inorganic and organic powder such as talc, mica, sericite, synthetic fluorphlogopite, pearl pigments such as alumina, barium sulfate, calcium secondary phosphate, calcium carbonate, coverage titanium oxide, finely divided titanium oxide, zirconium oxide, normal particle size zinc oxide, hydroxy apatite, iron oxide, iron titanate, ultramarine blue, Prussian blue, chromium oxide, chromium hydroxide, cobalt oxide, cobalt titanate, titanium oxide coated mica; organic powder such as polyester, polyethylene, polystyrene, methyl methacrylate resin, cellulose, 12-nylon, 6-nylon, styrene-acrylic acid copolymers, polypropylene, vinyl chloride polymer, tetrafluoroethylene polymer, boron nitride, fish scale guanine, laked tar color dyes, and laked natural color dyes. Such pigments may be treated with a hydrophobical treatment agent, including: silicone such as methicone, dimethicone, and perfluoroalkylsilane; fatty material such as stearic acid and disodium hydrogenated glutamate; metal soap such as aluminium dimyristate; aluminium hydrogenated tallow glutamate, hydrogenated lecithin, lauroyl lysine, aluminium salt of perfluoroalkyl phosphate, and aluminium hydroxide as to reduce the activity for titanium dioxide, and mixtures thereof. Such pigments may also be coated with substances considered more hydrophilic such as polysaccharides, caprylyl silane, or polyethylene oxide silane treatments.

Commercially available pigment powder component includes coverage titanium dioxide, such as SI-T-CR-50Z, SI-Titanium Dioxide IS, SA-Titanium Dioxide CR-50, SI-FTL-300 and SA/NAI-TR-10, all of them are available from Miyoshi Kasei, iron oxide and cyclopentasiloxane and dimethicone and disodium hydrogenated glutamate: SA/NAI-Y-10/D5(70%)/SA/NAI-R-10/D5(65%)/SA/NAI-B-10/D5 (75%) available from Miyoshi Kasei, iron oxide and disodium hydrogenated glutamate: SA/NAI-Y-10/SA/NAI-R-10/SA/NAI-B-10 available from Miyoshi Kasei, iron oxide and methicone: SI Mapico Yellow Light Lemon XLO/SI Pure Red Iron Oxide R-1599/SI Pure Red Iron Oxide R-3098/SI Pure Red Iron Oxide R-4098/SI Black Iron Oxide No. 247 available from Daito Kasei, alumina and titanium dioxide and methicone: SI-LTSG30AFLAKE H (5%) LHC available from Miyoshi Kasei, talc and methicone: SI-Talc JA13R LHC available from Miyoshi Kasei, mica and methicone: SI Mica available from Miyoshi Kasei, dimethicone: SA-SB-300 available from Miyoshi Kasei, mica and methicone: SI Sericite available from Miyoshi Kasei, mica and dimethicone: SA Sericite available from Miyoshi Kasei, mica and C9-15 Fluoroalcol Phosphates and Triethoxy Caprylylsilane: FOTS-52 Sericite FSE available from Daito Kasei, Talc and C9-15 Fluoroalcol Phosphates and triethoxy caprylylsilane: FOTS-52 Talc JA-13R available from Daito Kasei, boron nitride and methicone: SI02 Boron Nitride SHP-6 available from Daito Kasei, boron nitride and C9-15 fluoroalcol phosphates and triethoxy caprylylsilane: FOTS-52 Boron Nitride available from Daito Kasei, mica and titanium dioxide and methicone: SI Sericite TI-2 available from Miyoshi Kasei, mica and titanium dioxide and methicone: SI Mica TI-2 available from Miyoshi Kasei, talc and titanium dioxide and methicone: SI Talc TI-2 available from Miyoshi Kasei, lauroyl lysine: AMIHOPE LL available from Ajinomoto, synthetic fluorphlogopite and methicone: PDM-5L(S)/PDM-10L(S)/PDM-20L(S)/PDM-40L(S) available from Topy Industries.

Adhesive Agents

The compositions of the present invention can comprise from about 0.1% to about 10%, preferably from about 0.1% to about 2% of an adhesive agent. The species and levels of the adhesive agents are selected to provide, for example, a more flexible, longer-lasting benefit to composition, and/or better compatibility with other skin care or cosmetic formulations.

Examples of suitable adhesive agents include polyurethanes, including Polyderm PE-PA, available from Alzo International Inc.; co-polymerized amido ester compounds, including Polyderm PPG-17, available from Alzo International Inc.; and Acrylic Latex Dispersions.

Skin Active Agents

The compositions of the present invention may comprise a skin active agent which provides a particular skin care benefit characteristic of the usage of the skin care product. Herein, skin care benefit may include benefits related to appearance or make-up of the skin. The skin care active can provide acute (immediate and short lived) benefits, or chronic (long term and longer lasting) benefits.

The term "skin active agent" as used herein, means an active ingredient which provides a cosmetic and/or therapeutic effect to the area of application on the skin. The skin active agents useful herein include skin lightening agents, anti-acne agents, emollients, non-steroidal anti-inflammatory agents, topical anaesthetics, artificial tanning agents, anti-microbial and anti-fungal actives, skin soothing agents, sun screening agents, skin barrier repair agents, anti-wrinkle agents, anti-skin atrophy actives, lipids, sebum inhibitors, sebum inhibitors, skin sensates, protease inhibitors, anti-itch agents, hair growth inhibitors, desquamation enzyme enhancers, anti-glycation agents, and mixtures thereof. When included, the present composition comprises from about 0.001% to about 20%, preferably from about 0.1% to about 10% of at least one skin active agent.

The type and amount of skin active agents are selected so that the inclusion of a specific agent does not affect the stability of the composition. For example, hydrophilic agents may be incorporated in an amount soluble in the aqueous phase, while lipophilic agents may be incorporated in an amount soluble in the oil phase.

Other skin active agents purported to exhibit expression-line relaxing benefits for use in the present invention include, but are not limited to, Lavandox available from Barnet Products Corporation; Thallasine 2, available from BiotechMarine; Argireline NP, available from Lipotec; Gatuline In-Tense and Gatuline Expression, available from Gattefosse; Myoxinol LS 9736 from BASF Chemical Company, Syn-ake, available from DSM Nutritional Products, Inc.; and Instensyl®, available from Silab, Inc; Sesaflash™, available from Seppic Inc.

Skin lightening agents useful herein refer to active ingredients that improve hyperpigmentation as compared to pre-treatment. Useful skin lightening agents herein include ascorbic acid compounds, vitamin $B_3$ compounds, azelaic acid, butyl hydroxyanisole, gallic acid and its derivatives, glycyrrhizinic acid, hydroquinone, kojic acid, arbutin, mulberry extract, and mixtures thereof. Use of combinations of skin lightening agents is believed to be advantageous in that they may provide skin lightening benefit through different mechanisms.

Ascorbic acid compounds useful herein include ascorbic acid per se in the L-form, ascorbic acid salt, and derivatives thereof. Ascorbic acid salts useful herein include, sodium, potassium, lithium, calcium, magnesium, barium, ammonium and protamine salts. Ascorbic acid derivatives useful herein include, for example, esters of ascorbic acid, and ester salts of ascorbic acid. Particularly preferred ascorbic acid compounds include 2-o-D-glucopyranosyl-L-ascorbic acid, which is an ester of ascorbic acid and glucose and usually referred to as L-ascorbic acid 2-glucoside or ascorbyl glucoside, and its metal salts, and L-ascorbic acid phosphate ester salts such as sodium ascorbyl phosphate, potassium ascorbyl phosphate, magnesium ascorbyl phosphate, and calcium ascorbyl phosphate. Commercially available ascorbic compounds include magnesium ascorbyl phosphate available from Showa Denko, 2-o-D-glucopyranosyl-L-ascorbic acid available from Hayashibara and sodium L-ascorbyl phosphate with tradename STAY C available from Roche.

Vitamin $B_3$ compounds useful herein include, for example, those having the formula:

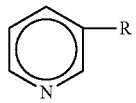

wherein R is —$CONH_2$ (e.g., niacinamide) or —$CH_2OH$ (e.g., nicotinyl alcohol); derivatives thereof; and salts thereof. Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide. Preferred vitamin $B_3$ compounds are niacinamide and tocopherol nicotinate, and more preferred is niacinamide. In a preferred embodiment, the vitamin $B_3$ compound contains a limited amount of the salt form and is more preferably substantially free of salts of a vitamin $B_3$ compound. Preferably the vitamin $B_3$ compound contains less than about 50% of such salt, and is more preferably essentially free of the salt form. Commercially available vitamin $B_3$ compounds that are highly useful herein include niacinamide USP available from Reilly.

Other hydrophobic skin lightening agents useful herein include ascorbic acid derivatives such as ascorbyl tetraisopalmitate (for example, VC-IP available from Nikko Chemical), ascorbyl palmitate (for example available from Roche Vitamins), ascorbyl dipalmitate (for example, NIKKOL CP available from Nikko Chemical); undecylenoyl phenyl alanine (for example, SEPIWHITE MSH available from Seppic); octadecenedioic acid (for example, ARLATONE DIOIC DCA available from Uniquema); *oenothera biennis* sead extract, and *pyrus malus* (apple) fruit extract, Water and Myritol 318 and butylene glycol and tocopherol and sscorbil tetraisopalmitate and Paraben and Carbopol 980 and DNA/ SMARTVECTOR UV available from COLETICA, magnesium ascorbyl phosphate in hyaluronic filling sphere available from COLETICA, and mixtures thereof.

Other skin active agents useful herein include those selected from the group consisting of N-acetyl D-glucosamine, panthenol (e.g., DL panthenol available from Alps Pharmaceutical Inc.), tocopheryl nicotinate, benzoyl peroxide, 3-hydroxy benzoic acid, flavonoids (e.g., flavanone, chalcone), farnesol, phytantriol, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, retinyl esters (e.g., retinyl propionate), phytic acid, N-acetyl-L-cysteine, lipoic acid, tocopherol and its esters (e.g., tocopheryl acetate: DL-α-tocopheryl acetate available from Eisai), azelaic acid, arachidonic acid, tetracycline, ibuprofen, naproxen, ketoprofen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neomycin sulfate, theophylline, and mixtures thereof. In a preferred example, the content level of a skin active agent is from about 0.001% to about 20%, more preferably from about 0.1% to about 10%

Optional Components

The compositions hereof may further contain additional components such as those conventionally used in topical products, e.g., for providing aesthetic or functional benefit to the composition or skin, such as sensory benefits relating to appearance, smell, or feel, therapeutic benefits, or prophylactic benefits (it is to be understood that the above-described required materials may themselves provide such benefits).

These components may include, but are not limited to, materials purported to smooth, firm or lift sagging or wrinkled skin including: Quicklift, available from BASF Chemical Company; Syntran PC5100, available from Interpolymer Corporation; Glycolift, available from Solabia USA Inc.; Alguard, available from Frutarom; Easyliance, from Soliance; and Phytodermina Lifting code 9002, available from Istituto Ricerche Applicate.

The CTFA Cosmetic Ingredient Handbook, Second Edition (1992) describes a wide variety of nonlimiting cosmetic and pharmaceutical ingredients commonly used in the industry, which are suitable for use in the topical compositions of the present invention. Such other materials may be dissolved or dispersed in the composition, depending on the relative solubilities of the components of the composition.

UV Protection Powder

UV protection powder provides UV protection benefit in the composition. UV protection powder has a particle size of less than 100 nm, which size provide very little coverage effect to the skin. The composition of each layer of the present invention may comprise from about 0% to about 20%, preferably from about 0.1% to about 10% of a UV protection powder, such as micronized titanium dioxide and micronized zinc oxide. The powder included in the pigment component herein is typically hydrophobic in nature, or hydrophobically treated.

Commercially available UV protection powder is titanium dioxide and methicone SI-TTO-S-3Z available from Miyoshi Kasei, titanium dioxide and dimethicone and aluminum hydroxide and stearic acid: SAST-UFTR-Z available from Miyoshi Kasei, Zinc oxide: Finex series available from Sakai Chemical Industry.

UV Absorbing Agent

The compositions of the present invention may comprise a safe and effective amount of a UV absorbing agent. A wide variety of conventional UV protecting agent are suitable for use herein, such as those described in U.S. Pat. No. 5,087,445, Haffey et al, issued Feb. 11, 1992; U.S. Pat. No. 5,073,372, Turner et al, issued Dec. 17, 1991; U.S. Pat. No. 5,073,371, Turner et al., issued Dec. 17, 1991; and Segarin, et al, at Chapter VIII, pages 189 et seq., of Cosmetics Science and Technology (1972). When included, the present composition comprises from about 0.5% to about 20%, preferably from about 1% to about 15% of a UV absorbing agent.

UV absorbing agent useful herein includes, for example, 2-ethylhexyl-p-methoxycinnamate (commercially available as PARSOL MCX), butylmethoxydibenzoyl-methane, 2-hydroxy-4-methoxybenzo-phenone, 2-phenylbenzimidazole-5-sulfonic acid, octyldimethyl-p-aminobenzoic acid, octocrylene, 2-ethylhexyl N,N-dimethyl-p-aminobenzoate, p-aminobenzoic acid, 2-phenylbenzimidazole-5-sulfonic acid, octocrylene, oxybenzone, homomethyl salicylate, octyl salicylate, 4,4'-methoxy-t-butyldibenzoylmethane, 4-isopropyl dibenzoylmethane, 3-benzylidene camphor, 3-(4-methylbenzylidene) camphor, Eusolex™ 6300, Octocrylene, Avobenzone (commercially available as Parsol 1789), and mixtures thereof.

Thickener

Useful for the present invention is a thickener. Thickeners can be used for solidifying solid water-in-oil form compositions of the present invention. When used, the thickener is kept to about 15% of the composition. The thickeners useful herein are selected from the group consisting of fatty compounds, gelling agents, inorganic thickeners and mixtures thereof. The amount and type of thickeners are selected according to the desired viscosity and characteristics of the product. These characteristics may include a synergistic effect between the thickener and the film forming ingredients, thereby enhancing product/film adhesion, contraction, or flexibility, while decreasing whiteness.

Thickening agents which can be used in the present invention include, but are not limited to, cross-linked polyacrylates such as Carbopol™ (Goodrich); polyacrylate copolymers such as SepiMAX ZEN (Seppic, Inc.); modified acrylate copolymers such as Sepiplus S (Seppic, Inc.) polymeric carboxylates including modified and unmodified starches, polysaccharide gums such as xanthan gum (e.g. CP Kelco's Keltrol CGT and Keltrol T630, Jungbunzlauer's Xanthan Gum), dehydroxanthan gum (e.g. Amaze XT from AkzoNobei), gallactomanan (Solaguni Tara from and cellulose derivatives (e.g. Natrosol 250). Gums may also include, but are not limited to, crosslinked-xanthan gum hydroxypropyl xanthan gum, undecylenoyl xanthan gum, deacetylated xanthan gum, guar gum, cellulose gum, carrageenan, hydroxylpropyl methyl cellulose, and sodium carboxymethyl chitin.

Polymers useful herein include swellable, lightly to moderately crosslinked polyvinyl pyrrolidones (PVP) such as ACP-1120 (International Specialty Products), acrylate copolymers/crosspolymers/blends such as acrylate/steareth-20 itaconate copolymer (Structure 2001 from AkzoNobel), acrylates/C10-30 alkyl acrylates copolymer (Amaze XT from AkzoNobel), acrylic acid/VP crosspolymer (Ultrathix P100 from International Specialty Products).

Fatty compounds useful herein include stearic acid, palmitic acid, stearyl alcohol, cetyl alcohol, behenyl alcohol, stearic acid, palmitic acid, the polyethylene glycol ether of stearyl alcohol or cetyl alcohol having an average of about 1 to about 5 ethylene oxide units, and mixtures thereof. Preferred fatty compounds are selected from stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof.

The gelling agent useful as thickeners of the present invention include esters and amides of fatty acid gellants, hydroxy acids, hydroxy fatty acids, other amide gellants, and crystalline gellants. N-acyl amino acid amides useful herein are prepared from glutamic acid, lysine, glutamine, aspartic acid and mixtures thereof.

Radiant Powder

Radiant powder is a pigment that is particularly effective in providing radiant look to the skin, by having a gloss level of more than 7.0. Gloss level is a parameter which can be measured by a known method using the opacity charts available from THE LENETA COMPANY, Drawdown bar (0.003 μm and 0.006 μm), solvent (KP-545 available from Shin-Etsu Chemical Co., Ltd.), Gloss Checker IG-320 available from HORIBA.

The radiant powder useful herein includes pearl pigments, such as mica and titanium dioxide and dimethicone: SA-Timiron MP-1001 and SA-Flamenco Orange available from Miyoshi Kasei, Titanium Dioxide and Mica and Alumina and Silica and Demethicone/Methicone Copolymer and Iron Oxide: Relief Color Pink P-2 available from CATALYSTS & CHEMICALS IND. CO., LTD., mica, synthetic mica, boron nitride and specified particle talc having an average particle size of about 20 μm and a gloss level of about 7.2 (0.003 μm on white back), 33.0 (0.006 μm on white back), about 8.5 (0.003 μm on black back) and about 10.3 (0.006 μm on black back). Specified particle talc has a higher gloss level and a lower transparency level than normal particle talc. Specifically, the gloss level of specified particle talc is about 130% to 200% vs. normal particle talc and the transparency level of specified particle talc is about 10% to 100% vs. normal particle talc. Transparency level can be measured by a known method using the opacity charts available from THE LENETA COMPANY, Drawdown bar (0.003 μm and 0.006 μm), solvent (KP-545 available from Shin-Etsu Chemical Co., Ltd.), Spectraflash available from Datacolor. Commercially available specified particle talc is available from Miyoshi Kasei Inc. under the trade name of SI-TALC CT-20.

In a single layer formulation, because other powders, such as coverage titanium dioxide, contained in the formulation may overwhelm the radiant powder effect, to achieve the radiant look effect, a typical level of radiant powder is as high as 5%. In the present invention, by formulating the radiant powder mainly in the second layer and coverage titanium dioxide in the first layer, and providing the first and second layers in a manner such that they can be simultaneously applied on the skin, the skin care product of the present invention can provide satisfied radiant appearance effect with lower level of radiant powder. As a result, there is provided more flexibility in product formulation. Compared to a single layer product, a multiple layer product comprising lower level of radiant powder has a better spreadability and light feel on the skin. In a preferred example, the content level of radiant powder in the second layer is from about 5% to about 25%, more preferably from about 10% to about 20% by weight of the composition of the second layer. When calculated based on the total weight of the first layer and the second layer, the preferred content level of radiant powder is from about 0.5% to about 5%.

Soft Focus Powder

Soft focus powder is a pigment that is particularly effective in providing a soft focus effect to the composition, namely natural finish yet having good coverage for minimizing the appearance of skin troubles, when incorporated in a defined amount. Specifically, the soft focus powder herein must meet two parameter criteria to provide such an effect. First, both the Total Luminous Transmittance (Tt) and Diffuse Luminous Transmittance (Td) of the pigment are relatively high. The soft focus powder has a Total Luminous Transmittance (Tt) of from about 40 to about 94 and a Diffuse Luminous Transmittance (Td) of from about 28 to about 38. Without being bound by theory, it is believed that, by having such high Tt and Td values, the soft focus powder exhibits a high transparency, thereby providing an overall natural finish. Second, the soft focus powder has a relatively high Haze value {(Td/Tt)×100} of from about 32 to about 95. Without being bound by theory, it is believed that, by having such high Haze value, the contrast between lighted area of the skin and shaded area of the skin (such as pores and wrinkles) is minimized for reducing the appearance of the trouble areas.

Total Luminous Transmittance (Tt), Diffuse Luminous Transmittance (Td), and Haze value {(Td/Tt)×100} can be measured and calculated by the artisan by reference to ASTM D 1003-00 "Standard Test Method for Haze and Luminous Transmittance of Transparent Plastics". Although the pigments herein are not plastics, the same principles of this specific standard test can be applied.

The soft focus powder useful herein includes polymethyl/methacrylate (PMMA), silica, hybrid pigments such as alumina treated mica, titanium dioxide treated talc, titanium dioxide treated mica, vinyl dimethicone/methicone silsesquioxane crosspolymer, alumina, barium sulfate and synthetic mica. Commercially available soft focus powder useful herein includes alumina treated mica having the trade name SA Excel Mica JP2 available from Miyoshi Kasei, which has a Total Luminous Transmittance (Tt) of about 87, Diffuse Luminous Transmittance (Td) of about 28, and Haze value {(Td/Tt)×100} of about 32.

Similar to radiant powder, when formulated with coverage titanium dioxide in a single layer, the content level of a soft focus powder shall be as high as 5% to achieve noticeable natural look effect. However, in the present invention, by formulating soft focus powder mainly in the second layer and coverage titanium dioxide in the first layer, and providing the first and second layers in a manner such that they can be simultaneously applied on the skin, the skin care product of the present invention can provide satisfied natural look effect with relatively low level of soft focus powder. As a result, the cost of the product can be controlled while also providing more flexibility in product formulation. In a preferred example, the content level of soft focus powder in the second layer is from about 2% to about 25%, more preferably from about 5% to about 20% based on the composition of the second layer. When calculated on the basis of the total weight of the first layer and the second layer, the preferred content level of soft focus powder is from about 0.5% to about 4%, more preferably from about 1% to about 3%.

Silicone Elastomer

Soft focus silicone elastomer is crosslinked siloxane elastomer which is particularly effective in providing soft focus effect to the skin. In other words, when incorporated in a cosmetic product a defined amount of silicone elastomer, the silicone elastomer can provide natural finish yet having good coverage for minimizing the appearance of skin troubles. Specifically, silicone elastomer has lower matte level compared with other silicone oil. Matte level is a parameter reflecting soft focus effect, i.e. natural finish of a cosmetic material. The lower the matte level is, the better natural finish the material can provide. Matte level of silicone elastomer used in the present application is less than about 40. Matte level can be measured by the PG-1M gloss meter (Incidence angle/Reflection angle: 60/60°) made by Nihon Denshoku Kogyo. Commercially available silicone elastomer useful in the present application includes a silicone elastomer having the tradename KSG-16 available from Shinetsu, which has a matte level of about 37.

Silicone elastomer suitable for use herein can be emulsifying or non-emulsifying crosslinked siloxane elastomer or mixtures thereof. The term "non-emulsifying" as used herein, defines crosslinked organopolysiloxane elastomer from which polyoxyalkylene units are absent. The term "emulsifying" as used herein, means crosslinked organopolysiloxane elastomer having at least one polyoxyalkylene (e.g., polyoxyethylene or polyoxypropylene) unit. Non-emulsifying elastomer useful in the present invention is formed via crosslinking organohydroenpolysiloxane with an alpha, omega-diene. Emulsifying elastomer herein includes polyoxyalkylene modified elastomer formed via crosslinking from organohydrogenpolysiloxane with polyoxyalkylene diene or organohydrogenpolysiloxane containing at least one polyether group crosslinked with an alpha, omega-diene. Emulsifying crosslinked organopolysiloxane elastomer can notably be chosen from the crosslinked polymer described in U.S. Pat. Nos. 5,412,004, 5,837,793, and 5,811,487. In addition, an emulsifying elastomer comprised of dimethicone copolyol crosspolymer (and dimethicone) is available from Shin Etsu under the tradename KSG-21.

Non-emulsifying elastomer is dimethicone/vinyl dimethicone crosspolymer. Such dimethicone/vinyl dimethicone crosspolymer is supplied by a variety of suppliers including Dow Corning (DC 9040 and DC 9041), General Electric (SFE 839), Shin Etsu (KSG-15, 16, 18 [dimethicone/phenyl vinyl dimethicone crosspolymer]), and Grant Industries (GRANSIL™ line of elastomer). Cross-linked organopolysiloxane elastomer useful in the present invention and processes for making them are further described in U.S. Pat. Nos. 4,970,252, 5,760,116, and 5,654,362. Additional cross-linked organopolysiloxane elastomer useful in the present invention is disclosed in Japanese Patent Application JP 61-18708, assigned to Pola Kasei Kogyo KK. Commercially available elastomer preferred for use herein is Dow Corning's 9040 silicone elastomer blend, Shin Etsu's KSG-21, and mixtures thereof.

Similar to the radiant powder, when formulated with coverage titanium dioxide in a single layer, the content level of a silicone elastomer shall be as high as 10% to achieve noticeable natural look effect. However, in the present invention, by formulating a silicone elastomer mainly in the second layer and coverage titanium dioxide in the first layer, and providing the first and second layers in a manner such that they can be simultaneously applied on the skin, the skin care product of the present invention can provide satisfied natural look effect with lower level of silicone elastomer. As a result, the cost of the product can be controlled while also providing more flexibility in product formulation. In a preferred example, the content level of silicone elastomer in the second layer is from about 1% to about 20%, preferably from about 2% to about 15%. When calculated based on the total weight of the first layer and the second layer, the preferred content level of silicone elastomer is from about 0.5% to about 8%, more preferably from about 1% to about 5%.

Oil Absorbing Powder

Oil absorbing powder is a pigment that is particularly effective in absorbing oil, and thereby can be included in the present composition for absorbing excessive sebum from the skin. Specifically, the oil absorbing powder herein has an oil absorbency of at least about 100 ml/100 g, preferably at least about 200 ml/100 g. Oil absorbency is a unit well known to the artisan, and which can be measured via: JIS K5101 No. 21 "Test Method for Oil Absorbency Level".

Oil absorbing powder useful herein includes spherical silica, and methyl methacrylate copolymer. Commercially available spherical oil absorbing pigments useful herein include spherical silica with tradename SI-SILDEX H-52 available from Miyoshi Kasei, Inc. having an oil absorbency of more than 200 ml/100 g, vinyl dimethicone/methicone silsesquioxane crosspolymer with tradename KSP-100 and KSP-101 available from ShinEtsu Chemical having an oil absorbency of more than 200 ml/100 g, and methyl methacrylate copolymer with tradename SA-GMP-0820 available from GANZ Chemical and surface treated by Miyoshi Kasei, Inc. having an oil absorbency of more than 100 ml/100 g. Typically, inclusion of oil absorbing powder for oil shine control may provide a composition with unfavorable spreadability performance. However, in the present invention, by including oil absorbing powder mainly in the second layer, the unfavorable spreadability performance can be improved. In a preferred example, the content level of an oil absorbing powder in the second layer is from about 1% to about 10%, more preferably from about 3% to about 5%.

Sebum Solidifying Powder

Sebum solidifying powder useful herein include those comprising a base substance which is coated with low crystalline zinc oxide, amorphous zinc oxide, or mixtures thereof, wherein the zinc oxide is from about 15% to about 25% by weight of the sebum solidifying powder. The base substance may be any organic or inorganic substances that are useful for cosmetic use, including those listed below under "Pigment Powder Component". The sebum solidifying powder herein can be suitably made according to the methods disclosed in US 2002/0031534 A1, herein incorporated by reference. The sebum solidifying powder may be surface treated. The sebum solidifying powder useful herein have the ability to solidify sebum, i.e., are effective in adsorbing free fatty acid, diglyceride, and triglyceride, and solidifying them by forming zinc salts thereof, such that a film is formed within about 30 minutes. Moreover, the originally glossy sebum changes appearance into a matte film. Such capability can be distinguished from other oil absorbing powder, which are not selective in the type of oil to be absorbed, and do not form a film after absorbing oil, thus may leave glossy gels and pastes after absorbing the sebum. Change in appearance provides a noticeable signal to the user that sebum has been controlled. Sebum solidifying effect may be conveniently measured by mixing a certain amount of powder with a certain amount of artificial sebum, mixing for a certain period of time, and allowing standing until solidified or showing matte appearance. The time taken for the mixture to solidify or to change appearance is recorded. The shorter the time taken to solidify or change appearance, the higher the solidifying effect is of the powder.

Commercially available sebum solidifying powder useful herein includes mica coated with hydroxyapatite, 20% zinc oxide with tradename PLV-20, and the same powder surface treated with methicone with tradename SI-PLV-20, both available from Miyoshi Kasei, Inc. Typically, inclusion of sebum solidifying powder for oil shine control may provide a composition with unfavorable spreadability performance. However, in the present invention, by including sebum solidifying powder mainly in the second layer, the unfavorable spreadability performance can be improved. In a preferred example, the content level of sebum solidifying powder in the second layer is from about 0.2% to about 10%, preferably from about 1% to about 7%.

Methods of Treatment

Various methods of treatment, application, regulation, or improvement may utilize the aforementioned compositions. Application of the present compositions can occur on any skin surface of the body. Skin surfaces of the most concern tend to be those not typically covered by clothing such as facial skin surfaces, hand and arm skin surfaces, foot and leg skin surfaces, and neck and chest skin surfaces (e.g., décolletage). In particular, application may be on a facial skin surface including the forehead, perioral, chin, periorbital, nose, and/or cheek skin surfaces.

Many regimens exist for the application of the composition to the skin. The composition may be applied at least once a day, twice a day, or on a more frequent daily basis, during a treatment period. When applied twice daily, the first and second applications are separated by at least 1 to about 12 hours. Typically, the composition may be applied in the morning and/or in the evening before going out in public.

The step of applying the composition to the skin may be done by localized application to an area that contains wrinkles. In reference to application of the composition, the term "localized", "local", or "locally" mean that the composition is delivered the targeted area (such as an area of skin containing wrinkles) while minimizing delivery to skin surface not requiring treatment. The composition may be applied and lightly massaged into the skin. It is recognized that localized application does allow for a reasonable amount of the composition to be applied to areas adjacent the wrinkles to be treated (i.e., the composition is unlikely to be applied or to remain within the boundary of the wrinkles without some spreading). The form of the composition or the dermatologically acceptable carrier should be selected to facilitate localized application. While certain embodiments of the present invention contemplate applying a composition locally to a wrinkled area, it will be appreciated that compositions of the present invention can be applied more generally or broadly to one or more facial skin surfaces to reduce the appearance of wrinkles within those facial skin regions. Likewise, the compositions of the present invention can be applied as a continuous film, or in patterns. Striations, patterned spots or random application of the compositions may be desirable. Applicators, as described below, may be beneficial assisting in patterned deposition.

The regimen may optionally begin with a cleansing step. The consumer can wash her face with a suitable cleanser (e.g., Olay Purifying Mud Lathering Cleanser, available from The Procter & Gamble Company, Cincinnati, Ohio), and gently dry her skin with a towel. Another optional step to the treatment regimens of this invention include applying a moisturizer, examples of which are given below in Table 3 and are commercially available (e.g., Olay Natural White UV Moisturizing Lotion SPF 15, available from The Procter & Gamble Company, Cincinnati, Ohio). The moisturizer can be applied to the skin before the skin smoothing composition, after the skin smoothing composition, or both. This moisturizer may or may not contain oils or pigment. Another optional step to the treatment regimens of this invention include applying a make-up primer or color cosmetic examples of these are given and commercially available (e.g. Olay Simply Ageless Serum Primer, Covergirl Clean Liquid Makeup, Covergirl Simply Powder Foundation, available from The Procter & Gamble Company, Cincinnati, Ohio). As indicated in the examples, the color foundation step may be in a liquid, powder or transitional form. The extent of adhesion and contractile ability of the skin smoothing composition is dependent on the order of regimen product application to skin and compositions.

While some methods described herein contemplate applying the compositions of the present invention with an applicator, it will be appreciated that applicators are not required and the compositions of the present invention can also be applied directly by using one's finger or in other conventional manners.

EXAMPLES

Table 1 below gives seven Examples according to the present invention, compared to six commercially available products. Web sites for the five commercially available products are listed below Table 1.

TABLE 1

| Product | Monovalent Silicate (reported as SiO$_2$) % | Polyvalent Silicate % | Ratio of Monovalent Silicate (SiO2):Polyvalent Silicate | Total Glycol Level | Ratio of Total Silicate (Monovalent + Polyvalent):Total glycol |
|---|---|---|---|---|---|
| Example 1 | 1.0 | 0.5 | 2.0 | 8.1 | 0.2 |
| Example 2 | 1.0 | 1.2 | 0.8 | 3.0 | 0.7 |
| Example 3 | 0.7 | 0.4 | 1.8 | 6.3 | 0.2 |
| Example 4 | 1.6 | 2.2 | 0.7 | 7.4 | 0.5 |
| Example 5 | 3.0 | 3.0 | 1.0 | 3.0 | 2.0 |
| Example 6 | 1.0 | 0.5 | 2.0 | 8.1 | 0.2 |
| Example 7 | 1.0 | 0.5 | 2.0 | 8.1 | 0.2 |
| Commercially Available Products | | | | | |
| Hydroxatone Instant Effect | 1.4 | 5.2 | 0.3 | 1.3 | 5.1 |
| Serious Skin Care FIRMA-FACE XR ™ Skin Tightener | 3.5 | 10.0 | 0.4 | 0.2 | 67.5 |
| Peter Thomas Roth Instant FIRMx (G10-A25744-01) | 2.1 | 17.8 | 0.1 | 7.4 | 2.7 |
| Flawless Effect Instant Facial Wrinkle Remover + Free Rejuvenating Eye Cream (G10-A25744-02) | 2.2 | 5.4 | 0.4 | 4.3 | 1.8 |
| Renoir No Lines Wrinkle Cream Facelift in a Bottle | 4.7 | 8.0 | 0.6 | 4.8 | 2.6 |

Table 2 below lists measured values for Contraction, Whiteness, Loss of Contraction and a calculated value weighting all four previous components in a single Overall Performance score. The seven examples according to the present invention are compared to the six competitive products from Table 1. All values were measured at 70° F. and 40% relative humidity.

TABLE 2

| | Contraction (%) | Whiteness | Loss of Contraction (%) | Overall Performance Score |
|---|---|---|---|---|
| Example 1 | 82 | 27 | 3 | 2.3 |
| Example 2 | 70 | 26 | 0 | 2.1 |
| Example 3 | 61 | 25 | 0 | 2.0 |
| Example 4 | 94 | 29 | 9 | 2.6 |
| Example 5 | 100 | 40 | 4 | 3.3 |
| Example 6 | 71 | 27 | 9 | 2.3 |
| Example 7 | 58 | 25 | 0 | 2.2 |
| Commercially Available Products | | | | |
| Hydroxatone Instant Effect | 95 | 56 | 19 | 4.3 |
| Serious Skin Care FIRMA-FACE XR ™ Skin Tightener | 113 | 46 | 22 | 3.9 |
| Peter Thomas Roth Instant FIRMx | 141 | 59 | 100 | 5.7 |
| Flawless Effect Instant Facial Wrinkle Remover | 91 | 56 | 23 | 4.3 |
| Renoir No Lines Wrinkle Cream Facelift in a Bottle | 90 | 25 | 68 | 3.0 |

Table 3 below gives seven Examples according to the present invention.

TABLE 3

| Skin Smoothing Composition | Water | Magnesium Aluminum Silicate *A | Propylene Glycol | Butylene Glycol | Pentylene Glycol | Xanthan Gum *B | Sodium Silicate Solution *C | Iron Oxide Dispersion *D |
|---|---|---|---|---|---|---|---|---|
| Example 1 | Q.S. | 0.5 | 8.1 | — | — | 2.1 | 3.5 | <0.1 |
| Example 2 | Q.S. | 1.2 | 3.0 | — | — | 2.4 | 3.5 | <0.1 |
| Example 3 | Q.S. | 0.4 | 6.3 | — | — | 1.7 | 2.6 | <0.1 |
| Example 4 | Q.S. | 2.2 | 7.4 | — | — | 2.6 | 5.6 | <0.1 |
| Example 5 | Q.S. | 3.0 | 3.0 | — | — | 0.5 | 10.5 | <0.1 |
| Example 6 | Q.S. | 0.5 | — | 8.1 | — | 2.1 | 3.5 | <0.1 |
| Example 7 | Q.S. | 0.5 | — | — | 8.1 | 2.1 | 3.5 | <0.1 |

*A - Veegum HS, available from R. T. Vanderbilt Company, Inc, Norwalk, CN.

*B - Keltrol CGT, available from CP Kelco, Atlanta, GA.

*C - N Clear Sodium Silicate, available from PQ Corporation, Valley Forge, PA.

*D - GLW55GRAP, available from Kobo Products, Inc., South Plainfield, NJ.

For Examples 1-7, in a suitable container, combine the water and magnesium aluminum silicate. Hydrate the magnesium aluminum silicate by inputting sufficient energy in the form of heat and/or shear. When fully hydrated, cool to <30° C., then add propylene glycol to the container, stir until blended. Slowly add in xanthan gum and mix using a suitable mixer (e.g., propeller blade, IKA T25) until the xanthan gum is fully hydrated and batch appears homogenous. Blend in the sodium silicate, then iron oxide dispersion. Stir until homogeneous.

Test Methods

To measure "contraction", as used herein, one measures the distance in inches (in) between two ends of a foam substrate after treatment with a skin smoothing composition. The foam substrate is a 3 mm thick open-cell polyurethane commercially available from Filtrona Porous Technologies as Medisponge 50 PW (the low strain or Young's modulus of this foam is 38.248 kPa) cut to 1×4 cm. In a 70° F.+/−2° C., 40%+/−2% relative humidity environment, with the foam substrate on a Teflon coated surface, 150 µL of the skin smoothing composition is dotted evenly atop the substrate, then lightly (~30 g pressure) spread across the substrate to cover the entire surface. The treated substrate is then allowed to dry 24 hours in this constant temperature/humidity environment. Then the projected distance between the ends of the foam substrate is measured with a ruler in inches. This procedure is performed in replicates of 3 or more and the values averaged.

The identical procedure detailed in the previous paragraph is also performed simultaneously with the Example 5 formulation. This data is used to normalize foam lot variability differences.

Then the following math is performed: "Contraction"= $[1.6-(D_{sample}-D_{Example\ 5})/1.6]*100$, where $D_{sample}$ is the projected distance in inches of the sample of interest, and $D_{Example\ 5}$ is the projected distance in inches of Example 5. In this calculation the value 1.6 is used because it is the distance in inches of a foam strip devoid of contraction. Values greater than 100% indicate the sample has greater contraction than our reference point, Example 5; values less than 100% indicate the sample has less contraction than Example 5.

To measure the "loss of contraction," as used herein, one measures the distance in inches (in) between two ends of a foam substrate following treatment with a skin smoothing composition then repeated physical manipulation thereof. The treated foam substrates of the "contraction" method (described above) are repeatedly pressed into a flat orientation to determine the "loss of contraction". Subsequent to measuring "contraction", in a 70° F.+/−2° C., 40%+/−2% relative humidity environment, the treated foam substrates are placed singly, flat, between two glass microscope slides, then a 305 g weight applied atop the upper glass slide for 10 seconds. The weight is removed for 10 seconds, then applied and removed in the same 10 second increments 2 additional cycles. The foam substrate is removed from the glass slides, set on a Teflon-coated surface, then after 10 minutes, the projected distance in inches (in) between two ends of a foam substrate measured using a ruler. This projected distance is called $D_{sample\ post-insult}$. The "Loss of Contraction"= $(D_{sample}-D_{sample\ post-insult})/D_{sample}$.

To measure "Whiteness", as used herein, one measures the opacity or lightness/darkness intensity. For the purposes of the present invention, color is defined according to a value on the CIELAB color system, which is based on the XYZ color system, defined by the Commission Internationale de l'Eclairage (CIE system) to provide a manner of objectively representing perceived color and color differences. X, Y and Z can be expressed in a variety of manners, or "scales," one of which is the Hunter scale. The Hunter scale has three variables, L, a, and b, which correlate mathematically to X, Y and Z, as described by Robertson, A. R. in "The CIE 1976 Color Difference Formulas," Color Research Applications, vol. 2, pp. 7-11 (1977). The compositions of the present invention may be analyzed with a Microflash integrating sphere spectrophotometer from DataColor International, Lawrenceville, N.J., USA, which generates values for L, a, and b. The value for "a" correlates to a value along the red-green (horizontal) axis, and the value for "b" correlates to a value along the blue-yellow (vertical) axis. For example, a blue-colored sample will have a negative b-value, whereas a red-colored sample will have a positive a-value. A more positive or negative value represents a more intense color. The value for "L" is an indicator of lightness and/or darkness, and correlates to a value along the z-axis, which is perpendicular to both the horizontal and vertical axes. An "L" of 0 is black and 100 a diffuse white. It is "L" that is used as a determinant of the film's "whiteness."

To measure the whiteness of a film it must first be drawn. Herein, "drawn" means that the composition is applied onto at least a portion of the black portion of an opacity chart (Form 2A, Leneta Company of Manwah, N.J. or the equivalent thereof, of which the top half is black and the bottom half is white) and spread into a film having a thickness of approximately 0.003 inches using a film applicator (e.g., as commercially available from BYK Gardner of Columbia, Md., or the equivalent thereof). The whiteness is then measured on the black portion of the opacity chart after the drawn film is allowed to dry for 24 hours under conditions of 70° F.+/−2° C., 40%+/−2% relative humidity using a spectrophotometer (e.g., Microflash integrating sphere spectrophotometer, specular-reflections included). Again, whiteness is used in reference to the "L" value of the drawn films. A higher number indicates the product looks white against the black background, while a lower number indicates the product is less white and/or more translucent, allowing greater visibility of the black background. Whiteness determinations are performed in replicates of 2.

The term "Overall Performance Score" is calculated using the contraction, whiteness, and loss of contraction data. The Overall Performance Score is calculated using the following equation, Overall Performance Score=(Contraction/100)+ (Whiteness/18)+(% Loss of Contraction/100)). For example, for Example 1 this is (82/100)+(27/18)+(3/100)=2.3. In this equation the whiteness value is divided by 18 as this is the approximate value of a completely invisible film.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin smoothing composition that comprises sodium silicate, polyvalent silicate which is a hydrated magnesium aluminum silicate, and water carrier, the skin smoothing composition forms a film having a thickness of from about 5 microns to about 50 microns, when applied to an area of skin having wrinkles the skin smoothing composition comprising:
   a) from about 0.5 to about 4% sodium silicate as measured by silica content (SiO2);
   b) from about 0.1% to about 4.0% of a polyvalent silicate which is a hydrated magnesium aluminum silicate which is stable in compositions having a pH greater than 10;
   c) from about 10 to 98% water; and
   d) from about 1% to about 20% of a plasticizer; and
   wherein the ratio of the weight of the sodium silicate to the polyvalent silicate is from about 1.0 to about 3.0 and the ratio of total silicate to plasticizer is equal to or less than 1.8 and the composition is in the form of a gel or oil-in-water emulsion; and wherein the pH of the composition is greater than 10.

2. The skin smoothing composition of claim 1, wherein the polyvalent silicate is a silicate clay selected from the group consisting of bentonite, laponite, smectite, kaolinite and mixtures thereof.

3. The skin smoothing composition of claim 1, wherein the plasticizer is an alkyl monoglycol or di-glycol.

4. The skin smoothing composition of claim 1, wherein the plasticizer structure contains 3 to 5 carbon atoms.

5. The skin smoothing composition of claim 1, wherein the plasticizer is propylene glycol.

6. The skin smoothing composition of claim 1, wherein the skin smoothing composition further comprises at least one polysaccharide thickener.

7. The skin smoothing composition of claim 6, wherein the polysaccharide thickener is xanthan gum.

8. The skin smoothing composition of claim 1, wherein the skin smoothing composition further comprises from about 0.001% to about 5% of a particulate material selected from the group consisting of colored and uncolored pigments, interference pigments, inorganic powders, organic powders, composite powders, optical brightener particles, and mixtures thereof.

9. The skin smoothing composition of claim 1, wherein the skin smoothing composition further comprises at least one skin care active.

10. The skin smoothing composition of claim 9, wherein the skin care active is selected from the group consisting of vitamin B compounds, vitamin C compounds, vitamin E compounds, peptides, sugar amines, natural botanical extract, oil control agents, skin lightening agents, and mixtures thereof.

11. The skin smoothing composition of claim 9, wherein the skin care active is selected from the group consisting of niacinamide, palmitoyl-lysine-threonine, palmitoyl-lysine-threonine-threonine-lysine-serine, N-acetyl-D-glucosamine, salicylic acid, dehydroacetic acid, sodium dehydroacetate, hexamidine compounds, and mixtures thereof.

* * * * *